United States Patent
Bobo

(10) Patent No.: US 6,183,421 B1
(45) Date of Patent: Feb. 6, 2001

(54) GAS COLUMN DEVICE WITH A SINGLE USE CONNECTOR

(76) Inventor: Donald Eugene Bobo, 18623 Santa Isadora St., FV, CA (US) 92708

(*) Notice: Under 35 U.S.C. 154(b), the term of this patent shall be extended for 0 days.

(21) Appl. No.: 09/379,283

(22) Filed: Aug. 20, 1999

(51) Int. Cl.$^7$ .................................................. A61B 5/02

(52) U.S. Cl. ............................................................ 600/486

(58) Field of Search .................................... 600/486, 587, 600/561, 485

(56) References Cited

U.S. PATENT DOCUMENTS

| | | |
|---|---|---|
| 5,573,007 | 11/1996 | Bobo . |
| 5,951,497 * | 9/1999 | Wallace et al. .................. 600/587 |
| 6,024,704 * | 2/2000 | Meador et al. .................. 600/486 |

* cited by examiner

*Primary Examiner*—Max Hindenburg
*Assistant Examiner*—Brian Szmal

(57) ABSTRACT

The present invention describes a connector set that joins the lumen of an air column catheter to a transducer housing. When first joined, the connector set automatically injects into the bladder an amount of air required for proper function of the bladder. At the same time, the connector set disables the mechanism used to inject air into the bladder and thereby limits the catheter to single patient use. The catheter connector provides an air vent to the ambient environment. The vent is closed by a pierceable seal. The transducer housing connector contains a piercing element that penetrates the vent seal when the connectors are mated. Though pierced, the vent seal retains its ability to prevent loss of air through the vent for the expected operating life of the catheter. Once the catheters are separated, the seal is irreparable breached. Should a second use be attempted, the breached seal allows gas that would otherwise be injected into the bladder to escape to the atmosphere. The bladder at this point can no longer be charged with gas and is unable to retain air pressure. The catheter cannot therefore be used a second time to couple pressure in the environment to a pressure transducer.

8 Claims, 4 Drawing Sheets

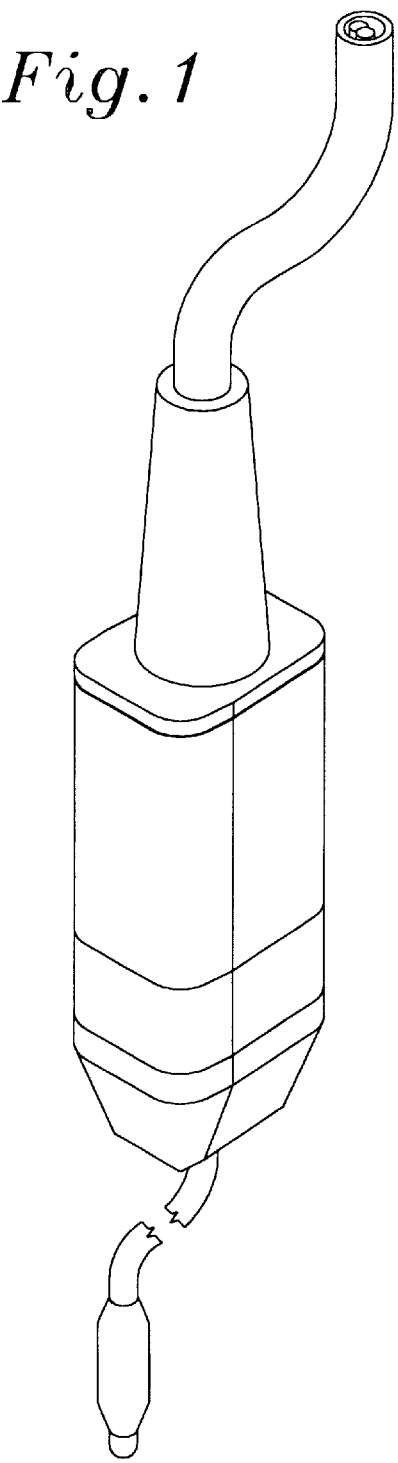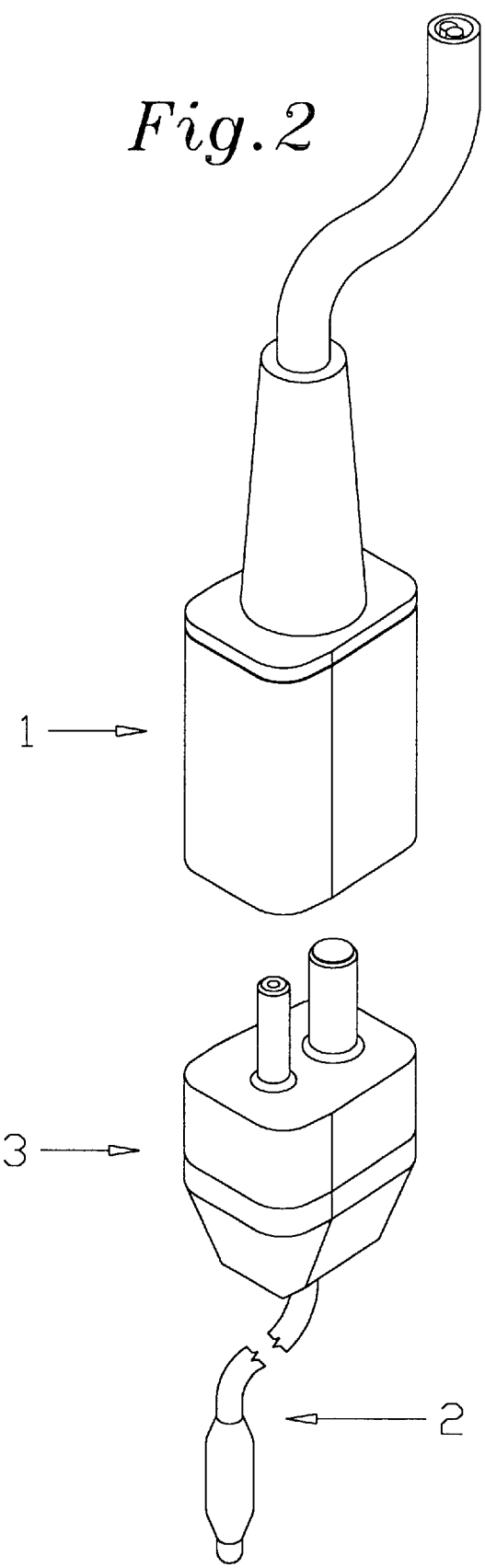
Fig.1
Fig.2

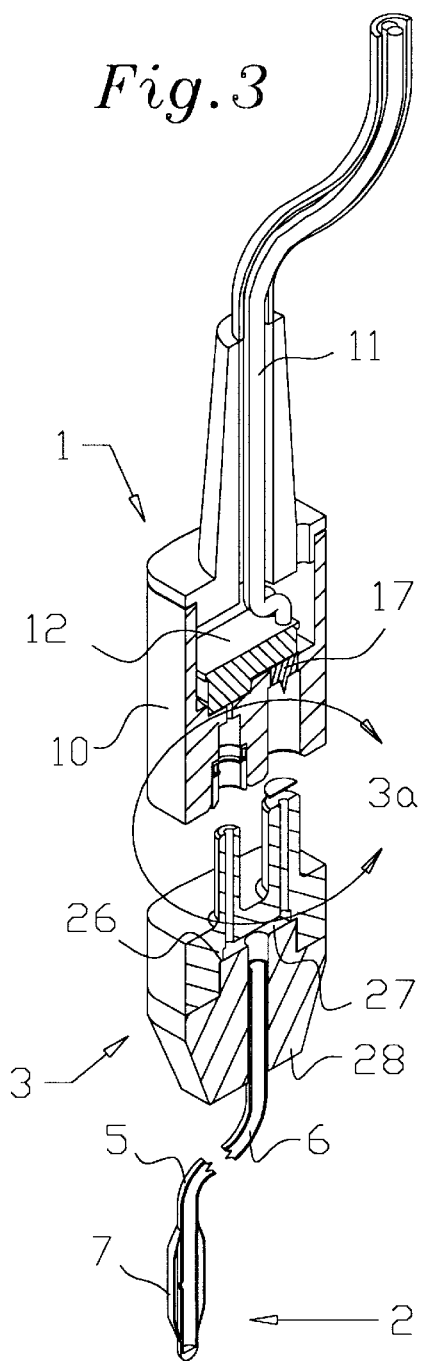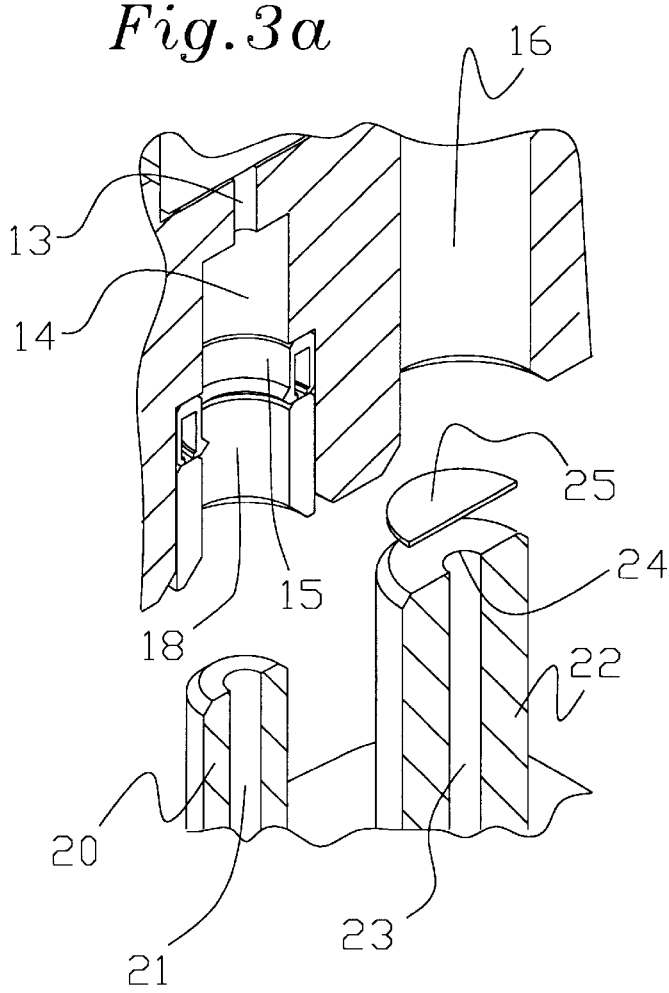

GAS COLUMN DEVICE WITH A SINGLE USE CONNECTOR

BACKGROUND OF THE INVENTION

1. Field of the Invention

This invention relates to a connector set that joins a gas column catheter to a pressure transducer airway in a manner that injects air into the catheter's bladder. The connectors ensure that the catheter is operable for no more than a single use.

2. Description of the Prior Art

Air column catheters have certain attributes that make them especially useful in measuring pressure in the body including natural body passageways such as the urethra or esophagus. These catheters may have a single bladder or a plurality of bladders, each of which is in communication with a dedicated pressure transducer. The bladder of an air column catheter can function for extended periods. It is therefore possible to use a gas column pressure-monitoring catheter in more than one patient. Reuse is not advisable, however, since a bladder will eventually fail and may do so in a manner that affects the accuracy of the pressure reading and the proper treatment of the patient. Consequently, there is a need to limit the use of an air-based catheter to a single patient.

There is little incentive to reuse most air column catheters that measure pressure in the body. Either the risk of infection is too great to justify reuse or the catheter has structural elements that make cleaning and resterilization quite difficult. Concern for infection is much less in the case of catheters introduced through natural body orifices such as the esophagus or the urethra. There is an economic incentive to reuse the catheter even though the manufacturer specifies that it is designed for single use. Reuse can lead to an uncontrolled situation where there is no awareness of the number of times the catheter has been reused. At some point, the bladder will leak and the catheter will no longer function properly. Since the leak may be small, it may not be obvious that the catheter is incapable of correctly reading pressure. If the observed pressure is incorrect, the patient may be mistreated based on invalid pressure values. The risk of bladder failure is proportional to the number of bladders on the catheter. For example, a urethra catheter may have two bladders on a measuring catheter and one on a separate reference catheter. A esophageal catheter may have four to six bladders.

U.S. Pat. No. 5,573,007 (Bobo) describes a connector and transducer housing that, when coupled, automatically injects air into a bladder of an air column catheter so as to make it operative.

SUMMARY OF THE INVENTION

The primary object of the connector system described in the present invention is to limit the use of a catheter to a single patient and thereby insure that the data obtained is accurate and valid for proper management of the patient. The invention is applicable to a system wherein the connection of the catheter to a transducer housing automatically injects air into the bladder of the pressure measuring system.

A related object of the present invention is to disable the mechanism used to inject air into the bladder at the same time as injecting air into the bladder for a single use, thereby preventing reuse.

In brief, the present invention describes a connector set that joins the lumen of an air column catheter to a transducer housing. When first joined, the connector set automatically injects into the bladder an amount of air required for proper function of the bladder. At the same time, the connector set disables the mechanism used to inject air into the bladder and thereby limits the catheter to single patient use. The catheter connector provides an air vent to the ambient environment. The vent is closed by a pierceable seal. The transducer housing connector contains a piercing element that penetrates the vent seal when the connectors are mated. Though pierced, the vent seal retains its ability to prevent loss of air through the vent for the expected operating life of the catheter. Once the catheters are separated, the seal is irreparably breached. Should a second use be attempted, the breached seal allows gas that would otherwise be injected into the bladder to escape to the atmosphere. The bladder at this point can no longer be charged with gas and is unable to retain air pressure. The catheter cannot therefore be used a second time to couple pressure in the environment to a pressure transducer.

The advantage of the present invention is that the pressure monitoring system is limited to a single use on one patient and not able to be reused on other patients, thereby eliminating the risk of endangering the health of patients by failure and false readings common to such devices when they are used repeatedly.

BRIEF DESCRIPTION OF THE DRAWINGS

These and other details of the invention will be described in connection with the accompanying drawings, which are furnished only by way of illustration and not in limitation of the invention, and in which drawings:

FIG. 1 is a perspective view of the preferred embodiment of the pressure measurement system;

FIG. 2 is an exploded view of the preferred embodiment of the pressure measurement system;

FIG. 3 is an exploded perspective view in partial cross section of the transducer housing particularly showing, a seal-piercing element;

FIG. 3a is an enlarged exploded perspective view in partial cross section, taken from 3a of FIG. 3, of the connector particularly showing a pierceable seal;

BEST MODE FOR CARRYING OUT THE INVENTION

Figure 4:
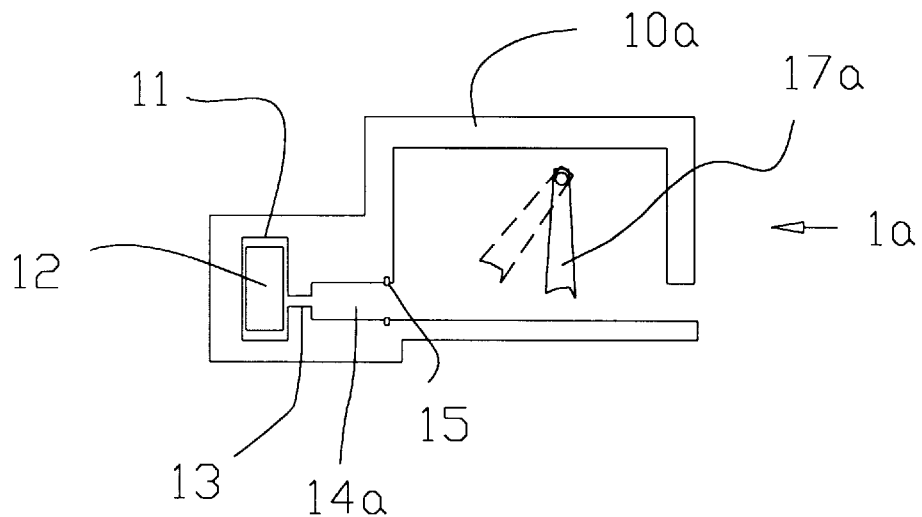
FIG. 4 is a cross-sectional view of an alternate embodiment of the pressure measurement system showing a transducer housing with a pivoting piercing element.

As seen in FIGS. 1 and 2, the invention consists of a transducer assembly 1 and a catheter assembly 2. As seen in FIGS. 3 and 3a, the distal end of the transducer housing of the transducer assembly is comprised of two cylinders, a pump cylinder 14 and a dummy cylinder 16. The pump cylinder communicates with a transducer 12 in the transducer assembly through a connecting lumen 13. The pressure signal generated by the transducer is conveyed by a cable 11 to a patient monitor (not shown), which displays pressure as a number and waveform as is well known in the art. The open end 18 of the pump cylinder contains a cylinder seal 15. As shown in FIG. 3. the seal forms a pneumatic seal with a pump piston 20, when the piston is inserted into the cylinder. Complete insertion of the piston causes the air residing in the cylinder to be injected into a bladder 7 by way of an air lumen 6. The proximal end of the dummy cylinder features a piercing element 17 that is used to pierce a vent seal 25 placed on the distal end of a dummy piston 22 having a dummy lumen 23 therethrough.

As seen in FIG. 3, the proximal end of a catheter assembly 2 is comprised of a connector assembly 3. The connector assembly has two pistons that extend from a connector base 26, a pump piston 20 and a dummy piston 22. Each piston has a through lumen that terminates in a plenum 27 formed by a connector base 26 and the distal surface of an adapter 28. The proximal end of a catheter 5 is bonded into the adapter 28. The adapter is then bonded into the base 26. The plenum 27 thereby communicates with an air lumen 6 of the catheter and the through lumen of each piston.

The distal end of the dummy piston lumen 23 provides a vent 24 that serves as an open passage to the atmosphere. A vent seal 25 closes the vent. Insertion of the catheter connector assembly into the transducer assembly causes the pump piston 20 to enter pump cylinder 14. As long as the vent at the distal end of the dummy piston is closed by a vent seal 25, the cylinder seal 15 causes the air displaced by the pump piston as it traverses the pump cylinder to be injected through the air lumen 6 of the catheter and into the bladder 7 of the catheter 5. Just before the mating of the connectors is compete, the piercing element located at the end of the dummy cylinder penetrates the vent seal. Although the vent seal is pierced in the connection process, the nature of the material used to form the seal is such that it conforms to the shape of the piercing element in an airtight manner and prevents air from escaping. The seal prevents air loss from the catheter during the expected operating life of the catheter. The air volume within the bladder is thereby preserved during the intended period of use.

The seal becomes incompetent when it is separated from the piercing element at the end of the procedure. If an attempt is made to use the catheter a second time, the air displaced by the piston pump will exit the vent rather than enter the bladder. The catheter is thereby made dysfunctional after a single use.

In operation, the connector set causes the air required by the bladder to be injected the first time the catheter is connected to the transducer housing. The connector set then disables the air injecting means and opens the catheter lumen to the atmosphere so the bladder cannot function once the catheter and transducer housing are separated.

The basic element of the invention is the incorporation of an air vent into the catheter's airway. The vent can be placed anywhere along an airway comprised of the catheter's lumen or its companion connector. The vent is sealed by a pierceable seal. The seal is breached during the insertion or removal of the connector set that joins the catheter to the transducer housing. Once breached, air that would otherwise be injected into the bladder to the atmosphere is diverted into the atmosphere. The catheter is thereby rendered dysfunctional. If the catheter has more than one bladder, the structure described can be applied to each lumen and pressure transducer combination.

There are a number of options concerning the location of the seal on the connector and the arrangement whereby the piercing element is caused to pierce the seal. For reasons of simplicity, the preferred embodiment is the design shown in FIGS. 1–3a. In this preferred embodiment, the catheter connector consists of a pump piston 20 and a dummy piston 22. Both pistons project upward from the connector base 26. Each piston has an air lumen with an open end that extends the length of the piston. When the catheter connector is mated to the transducer housing connector, the catheter's pump piston and dummy piston enter the transducer housing's pump cylinder and dummy cylinder. In the embodiment shown, the cylinder seal 15 is positioned in the distal end of the pump cylinder 14. The act of mating the connector displaces the air contained in the pump cylinder 14 into the bladder 7 of the catheter 5 as long as the vent seal 25 located at the end of the dummy piston is intact. A piercing element 17 located at the end of the dummy cylinder pierces the seal just before the connection is completed. The material used to make the seal has the ability to conform to the piercing element in a manner that prevents the escape of air between the seal and the element during a first use of the catheter. The air in the catheter is thus preserved during the period the catheter is in use. It has been found that a variety of films with moderate to good elasticity such as polyurethane or polyvinylchloride provides the sealing characteristics required for the vent seal 25. The thickness of the film is not critical and can vary from approximately 1 mm to 1 mm. The durometer is also not critical and can vary approximately 40–80A durometer.

If an attempt is made to use the catheter a second time, the invention will prevent the connecting process from injecting the amount of air required for proper operation of the bladder. Before the seal once again contacts the piercing element, most of the air displaced by the interaction of the pump piston 20 and the pump cylinder 14 will escape through vent 24 and into the atmosphere via. the annular space between the dummy cylinder 16 and the dummy piston 15. Since the seal is rendered incompetent after its initial separation from the piercing element a subsequent joining of the seal and the piercing element will not result in the injection of air into the bladder. The sequence of events insures that there is insufficient air available within the bladder to allow proper operation.

The dimensions of the dummy piston are not critical. The vent seal 25 can be formed in a variety of ways such as heat sealing a thin plastic film over the distal end of the dummy piston. It will be appreciated that the cylinder seal could be mounted on either the piston or the cylinder and still achieve the intended result.

While the device contains many specificities, these should not be construed as limitations of the scope of the invention, but rather as an exemplification of one preferred embodiment thereof. Many other variations are possible.

Figure 5:
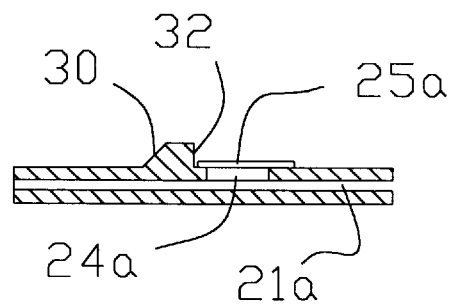
FIG. 5 is cross sectional view of the connector assembly used in the alternate embodiment.
Figure 5A:
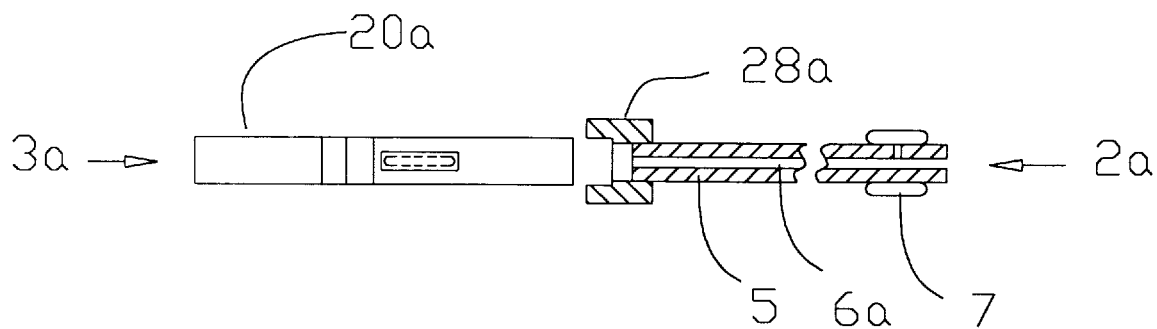
FIG. 5a shows an exploded view of the connector assembly and the catheter assembly.

In FIGS. 5 and 5a, an alternate embodiment of the present invention provides a connector assembly 2a with a single pump piston 20a with a pump piston lumen 21a that communicates with the air lumen 6 of the catheter. On the dorsal surface of the distal end of the connector 3a a protruding inclined plane along the top surface of the connector forms a ramp 30. The ramp declines abruptly to form a step 32. A vent hole 24a formed near the bottom of the step communicates between the air lumen 21a and the ambient atmosphere. A seal 25a is applied over the vent hole 24a. The piercing element 17a is a pivotable blade installed in the transducer housing in a manner wherein the blade is capable of pivoting in a plane parallel to the axis of the connector and the tip of the blade is capable of extending into the pathway of the connector such that tip can enter the vent hole.

Figure 6A:
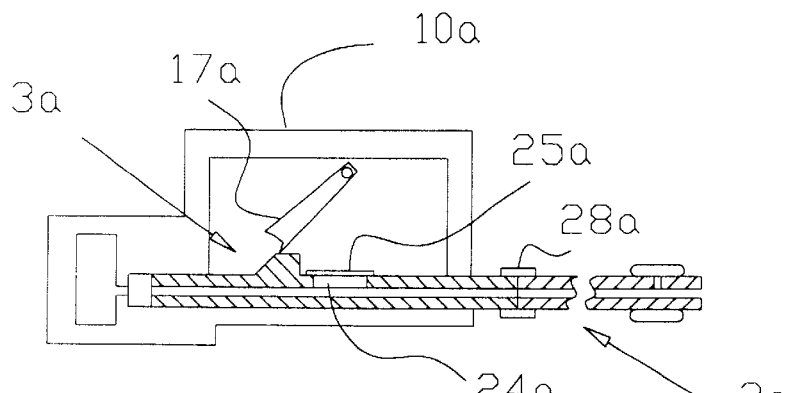
FIG. 6a–e shows the interaction of the pivoting piercing element as the connector is introduced and withdrawn from the transducer housing.
Figure 6B:
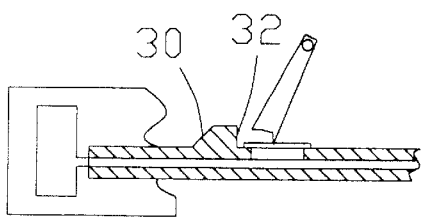
Figure 6C:
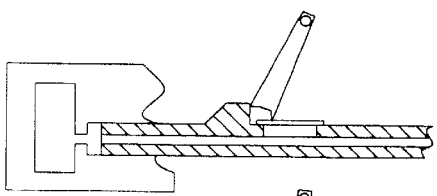
Figure 6D:
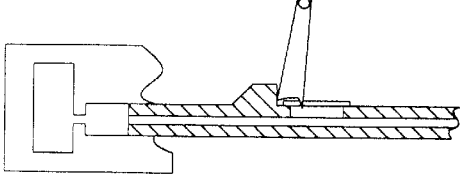
Figure 6E:
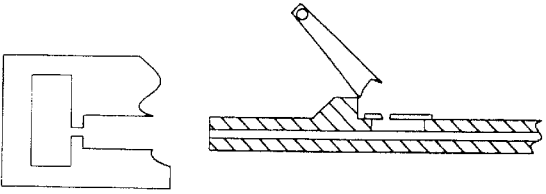

In operation, if it is assumed that the connector enters the transducer housing from right to left in a horizontal attitude, as shown in FIG. 6a, the ramp would push the blade up from its normal 6 o'clock position to an 8 o'clock position as the ramp of the connector passes by. When the step of the connector moves past the blade, the blade would drop down from and come to rest on the seal affixed to the vent hole as shown in FIG. 6b. The blade at this point would be resting in a 7 o'clock position. The contact pressure of the blade 17a against the seal 25a would be insufficient to penetrate the film material of the seal 25a; therefore the airway integrity would be preserved while the catheter is in use. Upon withdrawal of the connector, the blade would encounter the surface of the connector step as shown in FIG. 6c and be forced to pass through a 6 o'clock position which would cause the tip of the blade to pass through the plane of the seal as shown in FIG. 6c. In this manner the seal would be ruptured. The blade would continue to pivot as the connector is withdrawn until it rises to a 4 o'clock position so as to allow the connector to exit the transducer housing. Once ruptured, the vent would prevent the connector from injecting air into the bladder on subsequent connections.

Other mechanical schemes can be envisioned that implement the essence of the invention. This embodiment of the invention is an example of a construction that contains the three required elements of the invention. The first element requires that the catheter connector includes a seal that occludes a vent that communicates with the catheter lumen leading to the bladder. The second element requires that the seal integrity be preserved while the catheter is in use. The third element requires that the connection or disconnection of the catheter to the transducer housing results in the immediate or eventual breaching of the seal by a piercing element situated in the transducer housing. Once the seal is breached, subsequent attempts to use the catheter will cause the air displaced by the piston to escape into the atmosphere thereby rendering the catheter non-functional.

The present invention provides a simple, inexpensive yet effective device that precludes the reuse of an air column catheter and thereby eliminates the risk that a patient might be inappropriately managed due to inaccurate pressure data.

| List of Reference numbers |
| --- |
| 1. Transducer assembly |
| 2. Catheter assembly |
| 3. Connector assembly |
| 5. Catheter |
| 6. Air lumen |
| 7. Bladder |
| 10. Transducer housing |
| 11. Cable |
| 12. Transducer |
| 13. Connecting lumen |
| 14. Pump cylinder |
| 15. Cylinder seal |
| 16. Dummy cylinder |
| 17. Piercing element |
| 20. Pump piston |
| 21. Pump piston lumen |
| 22. Dummy piston |
| 23. Dummy piston lumen |
| 24. Vent |
| 25. Vent seal |
| 26. Connector base |
| 27. Plenum |
| 28. Adapter |
| 30. Ramp |
| 1.a Transducer assembly |
| 2.a Catheter assembly |
| 3.a Connector assembly |

| -continued |
| --- |
| List of Reference numbers |
| 6.a Air lumen |
| 10.a Transducer housing |
| 14.a Pump cylinder |
| 17.a Piercing element |
| 21.a Pump piston lumen |
| 24.a Vent |
| 25.a Vent seal |
| 28.a Adapter |

Elements of the alternative design that bear the same name as the preferred design are denoted by the letter a

What is claimed is:

1. A single use system for measuring the pressure in a mammalian body utilizing an air-bladder communicating with a catheter lumen in a catheter that relies upon the connection of the catheter to a transducer housing to activate the air bladder, the system comprising:

a transducer housing having a pressure transducer and having a means to activate the air bladder and a piercing element therein;

a catheter connector, having a lumen communicating with the catheter lumen and an air vent and an air vent seal occluding the air vent in the catheter connector and, the connector being insertable in the transducer housing so that the seal and piercing element will at some time become mutually engaged to cause the piercing element to breach the seal and the nature of contact between the seal and the piercing element is such that the seal is an effective pneumatic seal to ensure proper operation during the expected period of use the first time the connectors are joined, and so that the seal is no longer capable of occluding the vent thereafter when the two connectors are separated.

2. The system of claim 1 further comprising:

the catheter connector comprising a dummy piston having a dummy piston lumen therein in communication with the air vent having the occluding seal and a pump piston having a pump piston lumen therethrough, both the dummy piston lumen and the pump piston lumen communicating with the catheter lumen and the bladder;

the transducer housing comprising a dummy cylinder having a dummy cylinder lumen therein and a pump cylinder having a sealing element therein so that a pneumatic seal is provided between the pump piston and pump cylinder when the catheter connector is inserted into the transducer housing and the ingress of the pump piston into the pump cylinder displacing a quantity of air into the bladder;

the piercing element being positioned in the dummy cylinder so the piercing element is capable of piercing the seal on the air vent, so that completion of the connection of the catheter connector and the transducer housing causes the piercing element to pierce the occluding seal on the air vent and the occluding seal is sufficiently conformable to establish an airtight relationship with the surface of the piercing element when the seal is first penetrated by the element, so that upon separation of the two connectors the seal is rendered incompetent so as to air vent, the air displaced by the piston to the atmosphere in subsequent connection events.

3. The system of claim 2 wherein the piercing element is positioned relative to the occluding seal on the vent such that the pump piston has largely completed its passage within the pump cylinder before the piecing element encounters the occluding seal.

4. The system of claim 1 wherein the system comprises:

the transducer housing having a single pump cylinder with a transducer connecting lumen that communicates with the transducer, the piercing element being positioned within the transducer housing, the piercing element having a blade capable of being pivoted and a point capable of piercing the seal of the air vent;

the catheter connector having a single pump piston with a catheter connecting lumen that communicates with the catheter lumen, the catheter connector having the air vent formed in the catheter connector, the air vent communicating between the gas filled lumen of the catheter and the ambient atmosphere, the air vent occluded by the seal, the catheter connector having a means for pivoting the piercing element to prevent the piercing element from piercing the occluding seal during connection of the catheter connector and the transducer housing and during use of the system, the means for pivoting the piercing element being capable of causing the piercing element to pierce the occluding seal on the air vent upon disconnection of the catheter connector and the transducer housing.

5. The system of claim 4 wherein the means for pivoting the piercing element comprises a ramp on a dorsal surface of a distal end of the catheter connector, the ramp declining abruptly to form a step along the top surface of the connector, the catheter connector having the air vent formed at the bottom of the step so that the step pivots the blade so that the point will not pierce the seal on the air vent upon connecting the catheter connector to the transducer housing and the step causing the blade to pivot so that the point pierces the seal on the air vent upon di connecting the catheter connector from the transducer housing.

6. The system of claim 1 wherein the system comprises:

the catheter comprising a body having a proximal end, a distal end, and an outer surface suitable for insertion into the mammalian body, the catheter having a gas-filled lumen extending longitudinally through at least a portion of the length of the catheter body, the gas filled flaccid bladder positioned on the distal end of the gas filled lumen, the bladder being in gaseous communication with the lumen and being of a size capable of collapsing sufficiently to reflect the pressure within the body space in which it is placed, the gas filled lumen being thereby operable to transmit in the proximal direction changes in pressure exerted against the bladder;

the catheter connector mounted on the proximal end of the catheter suitable for insertion into a mating transducer connector in the transducer housing that communicates with the pressure transducer so that the catheter connector acts as a pump piston inserted into the mating transducer connector which acts as a pump cylinder to pump a quantity of gas into the bladder to fill the bladder.

7. A method for monitoring pressure within a mammalian body utilizing a single use connector system comprising a catheter, having a gas filled bladder and a catheter gas filled lumen communicating therewith, connectable to a transducer housing, having a transducer and a transducer gas filled lumen communicating therewith, the method comprising the steps of:

inserting a catheter connector, having an air vent communicating with the ambient environment and a pierceable seal covering the air vent, mounted on a proximal end of the catheter into a mating transducer connector in the transducer housing that communicates with the pressure transducer so that the catheter connector acts as a pump piston inserted into the mating transducer connector which acts as a pump cylinder interacting together as a means to pump a quantity of gas into the bladder to fill the bladder; the transducer housing further comprising a piercing element that is capable of piercing the seal at some point during use of the catheter connector, so that the nature of contact between the seal and the piercing element is such that the seal is an effective pneumatic seal so as to ensure proper operation during the expected period of use the first time the connectors are joined, and so that the seal is no longer capable of occluding the vent when the two connectors are separated;

withdrawing the connector from the housing so as to render the seal incompetent and unable to seal the catheter airway upon subsequent connections of the catheter and the transducer housing so as to render inoperative the means used to pump the quantity of gas into the bladder.

8. A method of creating a single use air-bladder based catheter that relies upon the connection of a catheter to a transducer housing to activate the air bladder, the method comprising the steps of:

inserting a connector, having an air vent and an air vent seal in the catheter airway, into a transducer housing having a piercing element so that the seal and piercing element will at some time become mutually engaged to cause the piercing element to breach the seal;

withdrawing the connector from the housing so as to render the seal incompetent and unable to seal the catheter airway upon subsequent connections of the catheter and the transducer housing so as to render inoperative the means used to inject air into the bladder.

* * * * *